US011484630B2

(12) United States Patent
Kota et al.

(10) Patent No.: US 11,484,630 B2
(45) Date of Patent: Nov. 1, 2022

(54) HEMOCOMPATIBILITY OF SUPERHEMOPHOBIC TITANIA SURFACES

(71) Applicant: Colorado State University Research Foundation, Fort Collins, CO (US)

(72) Inventors: Arun Kumar Kota, Fort Collins, CO (US); Ketul Popat, Fort Collins, CO (US); Sanli Movafaghi, Fort Collins, CO (US); Victoria Leszczak Murphy, Fort Collins, CO (US); Wei Wang, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 538 days.

(21) Appl. No.: 15/954,943

(22) Filed: Apr. 17, 2018

(65) Prior Publication Data

US 2018/0303981 A1    Oct. 25, 2018

Related U.S. Application Data

(60) Provisional application No. 62/487,711, filed on Apr. 20, 2017.

(51) Int. Cl.
*A61L 33/00* (2006.01)
*C01G 23/08* (2006.01)
(Continued)

(52) U.S. Cl.
CPC .......... *A61L 33/0017* (2013.01); *A61L 27/06* (2013.01); *A61L 27/50* (2013.01); *A61L 33/0076* (2013.01);
(Continued)

(58) Field of Classification Search
CPC .. A61L 33/0017; A61L 33/0076; A61L 27/50; A61L 2400/12; C01P 2004/62; C01P 2004/13
See application file for complete search history.

(56) References Cited

U.S. PATENT DOCUMENTS 3,415,109 A    12/1968    Sucker et al.
7,025,836 B1    4/2006    Zimmer et al.
(Continued)

FOREIGN PATENT DOCUMENTS

CN         103884755 A    6/2014

OTHER PUBLICATIONS

Bartlet et al., "Superhemophobic Titania Nanotube Array Surfaces for Blood Contacting Medical Devices," RSC Adv., 7:35466-35476, Jul. 2017.
(Continued)

*Primary Examiner* — Laura A Auer
(74) *Attorney, Agent, or Firm* — Haukaas Fortius PLLC; Michael H. Haukaas (57) ABSTRACT

In this work, we investigated the blood platelet adhesion and activation of truly superhemophobic surfaces and compared them with that of hemophobic surfaces and hemophilic surfaces. Our analysis indicates that only those superhemophobic surfaces with a robust Cassie-Baxter state display significantly lower platelet adhesion and activation. The understanding gained through this work will lead to the fabrication of improved hemocompatible, superhemophobic medical implants.

19 Claims, 7 Drawing Sheets

(51) Int. Cl.
  *A61L 33/04* (2006.01)
  *A61L 27/50* (2006.01)
  *A61L 33/02* (2006.01)
  *A61L 27/06* (2006.01)
  *C01G 23/053* (2006.01)

(52) U.S. Cl.
  CPC ............ *A61L 33/027* (2013.01); *A61L 33/04* (2013.01); *C01G 23/053* (2013.01); *C01G 23/08* (2013.01); *A61L 2300/202* (2013.01); *A61L 2300/42* (2013.01); *A61L 2400/12* (2013.01); *C01P 2002/85* (2013.01); *C01P 2004/02* (2013.01); *C01P 2004/03* (2013.01); *C01P 2004/13* (2013.01); *C01P 2004/30* (2013.01); *C01P 2004/62* (2013.01)

(56) References Cited

U.S. PATENT DOCUMENTS

| | | | |
|---|---|---|---|
| 8,081,308 B2 | 12/2011 | Wang et al. | |
| 8,574,704 B2 | 11/2013 | Smith et al. | |
| 9,181,455 B2 | 11/2015 | Liang | |
| 2007/0231542 A1* | 10/2007 | Deng | B08B 17/065 428/141 |
| 2010/0114514 A1 | 5/2010 | Wang et al. | |
| 2010/0279066 A1* | 11/2010 | Bulliard | B82Y 30/00 428/141 |
| 2013/0309450 A1 | 11/2013 | Khine et al. | |
| 2014/0011013 A1 | 1/2014 | Jin et al. | |
| 2014/0023852 A1 | 1/2014 | Bower et al. | |
| 2014/0200679 A1* | 7/2014 | Bluecher | A61L 27/50 623/23.74 |
| 2016/0153094 A1 | 6/2016 | Tuteja et al. | |
| 2016/0251803 A1 | 9/2016 | Tuteja et al. | |
| 2017/0022372 A1 | 1/2017 | Lynn et al. | |

OTHER PUBLICATIONS

Chu et al., "Superamphiphobic Surfaces," Chem. Soc. Rev., 43:2784-2798, Jan. 2014.
Kota et al., "Hierarchically Structured Superoleophobic Surfaces with Ultralow Contact Angle Hysteresis," Adv. Mater., 24:5838-5843, Aug. 2012.
Kota et al., "Superomniphobic Surfaces: Design and Durability," MRS Bulletin, 38(5):383-390, May 2013.
Kota et al., "The Design and Applications of Superomniphobic Surfaces," NPG Asia Materials, Jul. 2014, pp. 1-16.
Liao et al., "Liquid Droplet Movement on Horizontal Surface with Gradient Surface Energy," Sci. in China Series E: Technological Sciences, 49(6)733-741, Jan. 2006.
Liu et al., "Turning a Surface Superrepellent Even to Completely Wetting Liquids," Science, 342(6213):1096-1100, Nov. 2014.
Movafaghi et al., "Hemocompatibility of Superhemophobic Titania Surfaces," Adv Healthc Mater., 6(4), Feb. 2017, pp. 1-6.
Movafaghi et al., "Hemocompatibility of Superhemophobic Titania Surfaces," Supporting Information, Adv Healthc Mater., 6(4), Feb. 2017, pp. 1-11.
Movafaghi, et al., "Tunable Superomniphobic Surfaces for Sorting Droplets by Surface Tension," Lab Chip, 16:3204-3209, Jul. 2016.
Thampi, et al., "Do Liquid Drops Roll or Slide on Inclined Surfaces?," Langmuir, 29(10):3339-3346, Mar. 2013.
Wen et al., "Bioinspired Super-Wettability from Fundamental Research to Practical Applications," Angew Chem Int Ed Engl., 54(11):3387-3399, Mar. 2015.

* cited by examiner

HEMOCOMPATIBILITY OF SUPERHEMOPHOBIC TITANIA SURFACES

RELATED APPLICATIONS

This application claims priority under 35 U.S.C. § 119(e) to U.S. Provisional Patent Application No. 62/487,711, filed Apr. 20, 2017, which is incorporated herein by reference.

BACKGROUND OF THE INVENTION

Titanium-based implants have received a great deal of attention for their biocompatibility with many different tissues in the human body. However, when these implants come in contact with blood, platelet adhesion and activation occur, which may lead to further thrombosis and sometimes failure of these implants. It is well known that blood platelet adhesion and activation can be tailored by tuning the chemistry and texture of surfaces. One strategy that has been recently receiving attention is improving hemocompatibility (e.g., reduced platelet adhesion and activation) by employing superhydrophobic surfaces (i.e., surfaces that are extremely repellent to water).

Superhydrophobic surfaces display very high contact angles, typically >150° and very low roll off angles (i.e., the minimum angle by which the surface must be tilted relative to the horizontal for the droplet to roll off), typically <10° with water (a liquid with high surface tension, $\gamma_{lv}$=72.1 mN m$^{-1}$). However, superhydrophobic surfaces may not display high contact angles and more importantly very low roll off angles with blood (a liquid with relatively lower surface tension, $\gamma_{lv}$≈56 mN m$^{-1}$). In this context, we define superhemophobic surfaces as surfaces that display very high contact angles (>150°) and very low roll off angles (<10°) with blood. While there are a few studies investigating the hemocompatibility of superhydrophobic titania surfaces, it is not clear from the reports whether they are superhemophobic or not.

Accordingly, the fabrication of improved hemocompatible, superhemophobic medical implants would be beneficial to the medical field.

SUMMARY

In this work, for the first time, we investigated the blood platelet adhesion and activation of truly superhemophobic surfaces and compared them with that of hemophobic surfaces (i.e., surfaces display contact angles>90° with blood) and hemophilic surfaces (i.e., surfaces display contact angles<90° with blood). For each of our surfaces, we characterized the wettability using contact angle goniometry, the surface chemistry using X-ray photoelectron spectroscopy (XPS), and platelet adhesion and activation using fluorescence microscopy and scanning electron microscopy (SEM). Our results indicate that not all superhemophobic titania surfaces lead to significantly reduced platelet adhesion and activation. Our analysis indicates that only those superhemophobic surfaces with a robust Cassie-Baxter state display significantly lower platelet adhesion and activation compared to hemophobic and hemophilic surfaces. We envision that the understanding gained through this work will lead to the fabrication of improved hemocompatible, superhemophobic medical implants.

Accordingly, this disclosure provides a superhemophobic surface comprising:
a fluorinated titania surface having a textured morphology, wherein the fluorinated titania surface is superhemophobic to blood and has a Cassie-Baxter robustness factor (A*) of at least about 5 for blood;
wherein the % area of blood platelets ($f_{adh}$) that adhere to the fluorinated titania surface having a textured morphology is at least about 10% lower than the $f_{adh}$ of a fluorinated titania surface having a non-textured morphology.

The disclosure herein also provides a method of fabricating a biocompatible medical device comprising forming said superhemophobic surface on a medical device, wherein a medical device comprising said superhemophobic surface implanted in a subject is biocompatible with the subject and the formation of a blood clot on the medical device comprising the superhemophobic surface is negligible.

Additionally, this disclosure provides a method of fabricating a superhemophobic surface comprising:
a) anodizing a titanium substrate in an electrolyte comprising hydrofluoric acid to form a titania nanotube array;
b) annealing the titania nanotube array in a gas comprising oxygen; and
c) fluorinating the titania nanotube array to form a superhemophobic surface;
wherein the superhemophobic surface has a Cassie-Baxter robustness factor (A*) of at least about 5 for blood.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

The compositions and methods now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

Likewise, many modifications and other embodiments of the compositions and methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

The term "biocompatible" refers to materials that are not harmful to living tissue. Biocompatibility is related to the behavior of biomaterials and the ability of a material to perform with an appropriate host response in a specific situation, such as the quality of not having toxic or injurious effects on biological systems. For example, the ability of a biomaterial to perform its desired function with respect to a medical therapy, without eliciting any undesirable local or systemic effects in the recipient or beneficiary of that therapy but generating the most appropriate beneficial cellular or tissue response in that specific situation and optimizing the clinically relevant performance of that therapy. In another example, biocompatibility is the capability of a prosthesis implanted in the body to exist in harmony with tissue without causing deleterious changes (or the changes are so small and inconsequential that they are negligible).

The term "negligible" refers to an insignificant or unimportant change that is so small as to be not worth considering. For example, the percent area of blood platelets adhering to a superhemophobic surface may not be medically relevant, it may be no different than the percent area of blood platelets adhering to a control such as natural tissue or bone, it may be within the error of experimental determination, it may not result in the failure of the implant, it may not cause platelet activation or thrombosis, it may not have any medical consequences or adverse effects, or it ($f_{adh}$) may be less than 5%.

The term "blood" as used herein refers to the blood of any species, preferably mammals and more preferably primates, and even more preferably humans. The term refers to any component of blood, for example blood cell, blood plasma, erythrocytes, leukocytes, etc, but preferably platelets (or thrombocytes).

The term "texture" is the distribution of roughness or bumps or ridges or irregularities on the surface of a sample. A smooth texture would have a surface free from roughness or bumps or ridges or irregularities. A rough texture would have a surface comprising roughness or bumps or ridges or irregularities to varying degrees. The degree of texture is dependent on the size (e.g., height and inter-feature distance) of the roughness or bumps or ridges or irregularities. Texture is seen in almost all engineered materials and can have a great influence on materials properties. A complete lack of texture, for example, is a solid surface that is perfectly smooth down to the molecular scale. Texture can be determined by various methods. Some methods allow a quantitative analysis of the texture, while others are only qualitative. Among the quantitative techniques, the most widely used is an optical profilometer. Among the qualitative techniques, the most widely used is a Scanning Electron Microscope.

Embodiments of the Invention

This disclosure describes various embodiments of a superhemophobic surface comprising:
a fluorinated titania surface having a textured morphology, wherein the fluorinated titania surface is superhemophobic to blood and has a Cassie-Baxter robustness factor (A*) of at least about 5 for blood;
wherein the % area of blood platelets ($f_{adh}$) that adhere to the fluorinated titania surface having a textured morphology is at least about 10% lower than the $f_{adh}$ of a fluorinated titania surface having a non-textured morphology.

In some embodiments, the textured morphology has a feature diameter (2R) of about 1 µm or less than about 1 µm. In other embodiments, 2R is about 2 µm, about 1.5 µm, about 0.9 µm, about 0.8 µm, about 0.7 µm, about 0.6 µm, about 0.5 µm, about 0.4 µm, about 0.3 µm, about 0.2 µm, about 0.1 µm, or about 0.05 µm.

In some embodiments, the textured morphology has an inter-feature spacing (2D) of about 10 µm or less than about 10 µm. In other embodiments, 2D is about 9 µm, about 8 µm, about 7 µm, about 6 µm, about 5 µm, about 4 µm, about 3 µm, about 2 µm, about 1 µm, about 0.75 µm, about 0.5 µm, about 0.25 µm, or about 0.1 µm.

In other embodiments, the textured morphology has a feature diameter (2R) of about 0.05 µm to about 0.5 µm and an inter-feature spacing (2D) of about 0.05 µm to about 5 µm. In some other embodiments, the textured morphology is a nanoflower or a nanotube. In yet other embodiments, the fluorinated titania surface comprises a fluorinated ($C_8$-$C_{18}$) alkyl, for example, a heptadecafluoro-1,1,2,2-tetrahydrodecyl silane. In other embodiments the titania surface comprises a fluorinated alkyl, alkylsilane, ($C_8$-$C_{80}$)alkyl, or ($C_8$-$C_{80}$)alkylsilane.

In additional embodiments, the titania surface may be modified with various fluorinating agents such as, a fluoroalkyl silane, a perfluroalkyl silane, 1H,1H,2H,2H-perfluorooctylphosphate (PFOP), 1H,1H,2H,2H-perfluorooctanoic acid (PFOA), 1H,1H,2H,2H-perfluorooctyl trichlorosilane (PFOTS), 1H,1H,2H,2H-perfluorodecyl trichlorosilane (PFDTS), 1H,1H,2H,2H-perfluorodecane-1-thiol (PFDSH), 1H,1H,2H,2H-perfluorodecyl acrylate (PFDAE), perfluorooctyl trichlorosilane, a perfluorodecyl polyhedral oligomeric silsesquioxane (FluoroPOSS), perfluorinated phosphates, fluorinated thiols, fluorinated acids, fluorinated monomers, fluorinated polymers, or fluorinated copolymers.

In various embodiments, A* is about 50 to about 1000. In other embodiments, A* is about 10 to about 100, about 100 to about 200, about 200 to about 300, about 300 to about 400, about 400 to about 500, about 500 to about 600, about 600 to about 700, about 700 to about 800, about 800 to about 900, about 900 to about 1000, about 1000 to about 2000, about 5 to about 3000, about 5 to about 4000, about 5 to about 5000, about 5 to about 7,500, about 5 to about 10000, about 5,000 to about 20,000, about 5,000 to about 30,000, about 5,000 to about 40,000, about 5,000 to about 50,000, or about 5 to about 50,000.

In additional embodiments, the surface energy ($\gamma_{sv}$) of the superhemophobic surface is less than about 20 mN m$^{-1}$. In other embodiments, $\gamma_{sv}$ is less than about 100 mN m$^{-1}$, less than about 75 mN m$^{-1}$, less than about 50 mN m$^{-1}$, less than about 25 mN m$^{-1}$, or less than about 10 mN m$^{-1}$.

In various additional embodiments, the superhemophobic surface is biocompatible. In other various embodiments, a blood platelet that adheres to the fluorinated titania surface having a textured morphology does not manifest in platelet aggregation. In some other embodiments, a blood platelet that adheres to the fluorinated titania surface having a textured morphology does not manifest in dendritic extensions. In additional embodiments, a blood platelet that adheres to the fluorinated titania surface having a textured morphology does not manifest in platelet activation.

In yet some other embodiments, the % area of blood platelets ($f_{adh}$) that adheres to the fluorinated titania surface having a textured morphology is about 15% to about 95% lower than the $f_{adh}$ of a fluorinated titania surface having a non-textured morphology. In other embodiments, $f_{adh}$ is about 20% lower, about 25% lower, about 30% lower, about 40% lower, about 50% lower, about 60% lower, about 70% lower, about 75% lower, about 80% lower, about 85% lower, about 90% lower, or about 100% lower.

In other embodiments, the superhemophobic surface has a contact angle of greater than about 155°. In other embodiments, the contact angle is greater than about 145° to about 180°, about 150° to about 180°, or about 175° to about 180°.

In yet other embodiments, the superhemophobic surface has a roll off angle of less than about 5°. In other embodiments, the roll off angle of less than about 20°, less than about 15°, less than about 9°, less than about 8°, less than about 7°, less than about 6°, less than about 5°, less than about 4°, less than about 3°, less than about 2°, or less than about 1°.

This disclosure also provides additional embodiments of a method of fabricating a biocompatible medical device comprising forming the a superhemophobic surface described herein on a medical device, wherein a medical device comprising the superhemophobic surface implanted in a subject (in need thereof) is biocompatible with the subject and the formation of a blood clot on the medical device comprising the superhemophobic surface is negligible.

This disclosure also provides various additional embodiments of a method of fabricating a superhemophobic surface comprising:
  a) anodizing a titanium substrate in an electrolyte comprising hydrofluoric acid to form a titania nanotube array;
  b) annealing the titania nanotube array in a gas comprising oxygen; and
  c) fluorinating the titania nanotube array to form a superhemophobic surface;
wherein the superhemophobic surface has a Cassie-Baxter robustness factor (A*) of at least about 5 for blood.

In various embodiments the titania nanotube array, annealed titania nanotube array, or fluorinated titania nanotube array has a textured surface. In other embodiments the textured surface of the titanium substrate, or the anodized titanium substrate comprises a titania nanotube array, an annealed titania nanotube array, or a fluorinated titania nanotube array. In additional embodiments, the textured surface is superhemophobic, wherein the superhemophobic surface has a Cassie-Baxter robustness factor (A*) of about 5 to about 5,000 for blood, or about 5 to about 50,000 for blood.

In some embodiments, the % area of blood platelets ($f_{adh}$) that adheres to the superhemophobic surface is at least about 20% lower than the $f_{adh}$ of a fluorinated non-textured titania surface. In various other embodiments, a blood platelet that adheres to the superhemophobic surface does not manifest in platelet activation. In additional other embodiments, the formation of a blood clot on the superhemophobic surface is negligible.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

Results and Discussion

When a liquid droplet comes in contact with a non-textured (i.e., smooth) solid surface, it displays the Young's contact angle θ. Typically, a surface with θ>90° with water is considered hydrophobic and a surface with θ<90° with water is considered hydrophilic. Similarly, we consider a surface with θ>90° with blood hemophobic and a surface with θ<90° with blood hemophilic. Typically, surfaces with very low solid surface energy $\gamma_{sv}$ tend to display high contact angles. When the liquid droplet comes in contact with a textured (i.e., rough) solid surface, macroscopically, it displays an apparent contact angle θ*, and it can adopt one of the following two configurations to minimize its overall free energy—the Wenzel state or the Cassie-Baxter state. In the Wenzel state, the contacting liquid droplet completely permeates the surface protrusions thereby increasing the solid-liquid interfacial area. On the other hand, in the Cassie-Baxter state, the liquid does not completely wet the surface texture. Instead, pockets of air remain trapped underneath the liquid droplet introducing a composite liquid-air-solid interface. This greatly reduces the solid-liquid interfacial area, which in turn leads to high θ* and low roll off angles ω. Typically, the Cassie-Baxter state is preferred for designing super-repellent surfaces (e.g., superhydrophobic and superhemophobic surfaces). The Cassie-Baxter state can be obtained by combining a surface chemistry possessing a low solid surface energy with an appropriate texture.

The Cassie-Baxter state is a metastable state. When a sufficiently high pressure is applied on a liquid in the Cassie-Baxter state, the liquid will breakthrough, (i.e., permeate and fully wet the protrusions) thereby transitioning to the Wenzel state. The breakthrough pressure $P_{breakthrough}$ is the minimum pressure that can force such a transition from the Cassie-Baxter state to the fully wetted Wenzel state. In order to have effective super-repellence to liquids, it is essential to have a robust Cassie-Baxter state with high $P_{breakthrough}$. One measure of the robustness of Cassie- Baxter state is the robustness factor $A^*$. The robustness factor represents the ratio between the breakthrough pressure $P_{breakthrough}$ and reference pressure $P_{ref}=2\gamma_{lv}/l_{cap}$, where $l_{cap}=\sqrt{\gamma_{lv}/\rho g}$ is the capillary length, $\rho$ is the liquid density and g is the acceleration due to gravity. The reference pressure is approximately the minimum possible pressure difference across the composite interface for millimetric or larger liquid droplets or puddles on extremely non-wetting textured surfaces. For hexagonally packed textured surfaces composed of discrete pillars (such as the textures used in this work; see Example 6), the robustness factor $A^*$ is given as:

$$A^* \approx \left| \frac{\pi R l_{cap} \cos\theta}{2\sqrt{3}(R+D)^2} \right| \quad (6)$$

Here, 2R is the pillar diameter (i.e., feature size) and 2D is the inter-pillar spacing (i.e., spacing between features). Large values of $A^*$ ($A^* \gg 1$) imply a robust Cassie-Baxter state. On the other hand, values of $A^* < 1$ imply that the composite interface cannot maintain its stability against small pressure differentials across the liquid-vapor interface and the Cassie-Baxter state is not robust.

Figure 1:
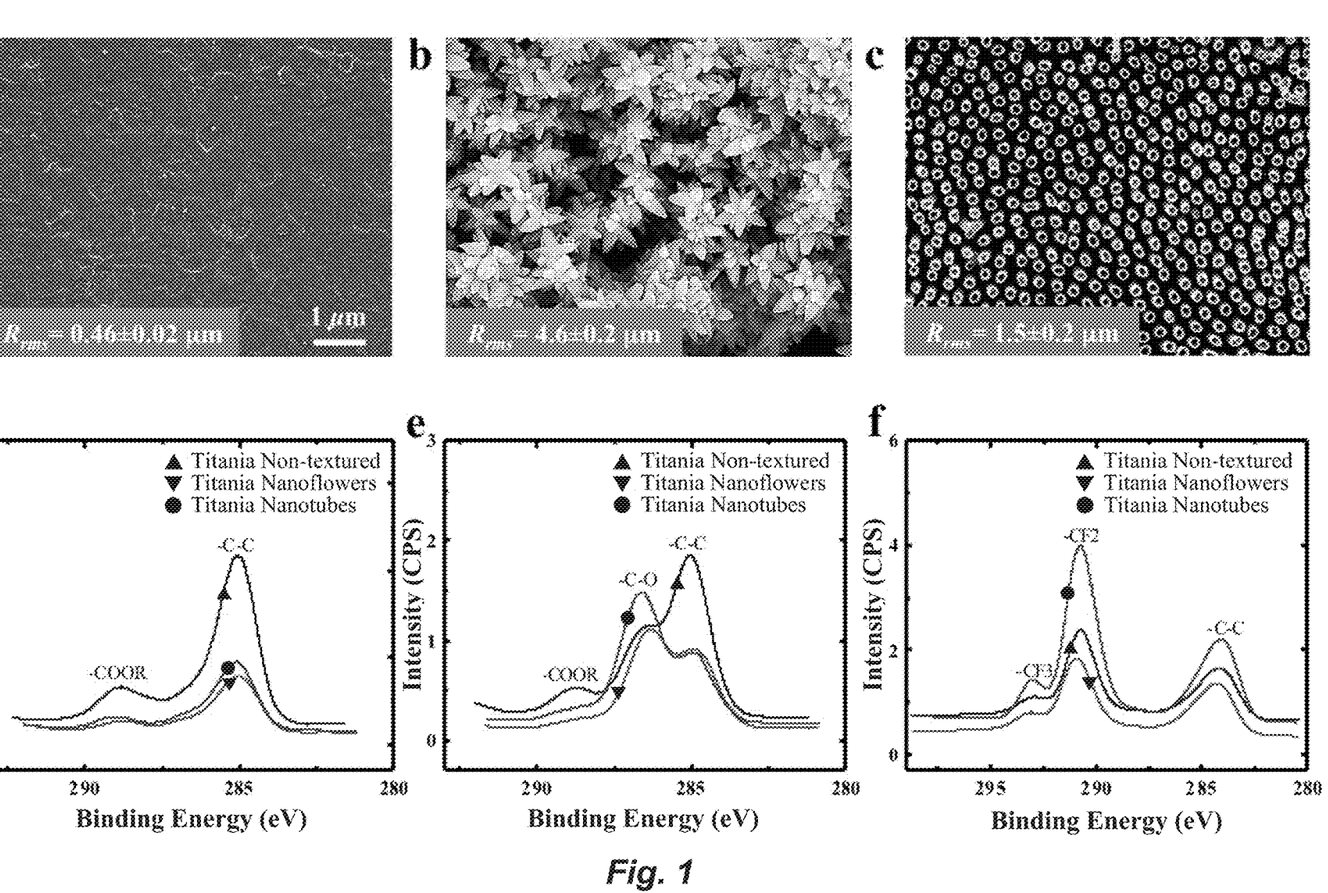
FIG. 1. SEM images showing the morphology of a) titania non-textured, b) titania nanoflowers and c) titania nanotubes. The root mean square roughness $R_{rms}$ of each surface is shown. d), e) and f) High resolution C1s XPS spectra for unmodified, PEGylated and fluorinated titania surfaces, respectively.

In this work, we fabricated superhemophobic titania surfaces with different values of $A^*$ and compared their platelet adhesion and activation with hemophobic and hemophilic surfaces. In order to fabricate the hemophilic, hemophobic and superhemophobic titania surfaces, we employed three different morphologies—non-textured, nanoflowers and nanotubes—and for each morphology, three different surface chemistries—unmodified, PEGylated and fluorinated. We synthesized the non-textured titania surfaces via oxidation, titania nanoflower surfaces via hydrothermal synthesis and titania nanotube surfaces via electrochemical anodization (see Example 3). SEM images show the nearly smooth morphology of non-textured titania surfaces (FIG. 1a), the textured morphology of titania nanoflowers with $2R \approx 1$ μm (FIG. 1b) and the textured morphology of titania nanotubes with $2R \approx 0.25$ μm (FIG. 1c). Subsequently, each titania morphology was left unmodified, PEGylated with a PEG silane and fluorinated with a fluorosilane (see Examples). We chose to PEGylate and fluorinate the surfaces because the steric repulsion induced by the water soluble PEG layer and the reduced interaction induced by the low solid surface energy of the fluorocarbons are known to reduce platelet adhesion and activation.

The high resolution C1s spectra (FIG. 1d, FIG. 1e and FIG. 10 indicate the presence of the characteristic —CO groups on PEGylated surfaces and the characteristic —$CF_2$ and —$CF_3$ groups on fluorinated surfaces. We characterized the wettability of all titania surfaces (i.e., different morphologies and surface chemistries) by measuring the contact angles and roll off angles of human blood plasma (Table 1). Based on the contact angles, all unmodified and PEGylated surfaces (non-textured, nanoflowers and nanotubes) are hemophilic, fluorinated non-textured surfaces are hemophobic, and fluorinated nanoflower and fluorinated nanotube surfaces are superhemophobic. Human blood plasma droplets are in the Wenzel state on the unmodified nanoflower and nanotube surfaces and the PEGylated nanoflower and nanotube surfaces. In contrast, human blood plasma droplets are in the Cassie-Baxter state on the fluorinated nanoflower and nanotube surfaces and consequently, these surfaces are superhemophobic. As might be anticipated, on superhemophobic titania surfaces, blood droplets can easily roll off.

TABLE 1

Contact angles and roll off angles of human blood plasma on all the titania surfaces fabricated in this work. NR implies no roll off.

| | Contact angles and roll off angles | | |
|---|---|---|---|
| | Non-textured | Nanoflower | Nanotube |
| Unmodified | θ = 61°, NR Hemophilic | θ* = 25°, NR Hemophilic | θ* = 30°, NR Hemophilic |
| PEGylated | θ = 31°, NR Hemophilic | θ* = 20°, NR Hemophilic | θ* = 18°, NR Hemophilic |
| Fluorinated | θ = 97°, NR Hemophobic | θ* = 161°, ω = 7° Superhemophobic | θ* = 159°, ω = 5° Superhemophobic |

Figure 2:
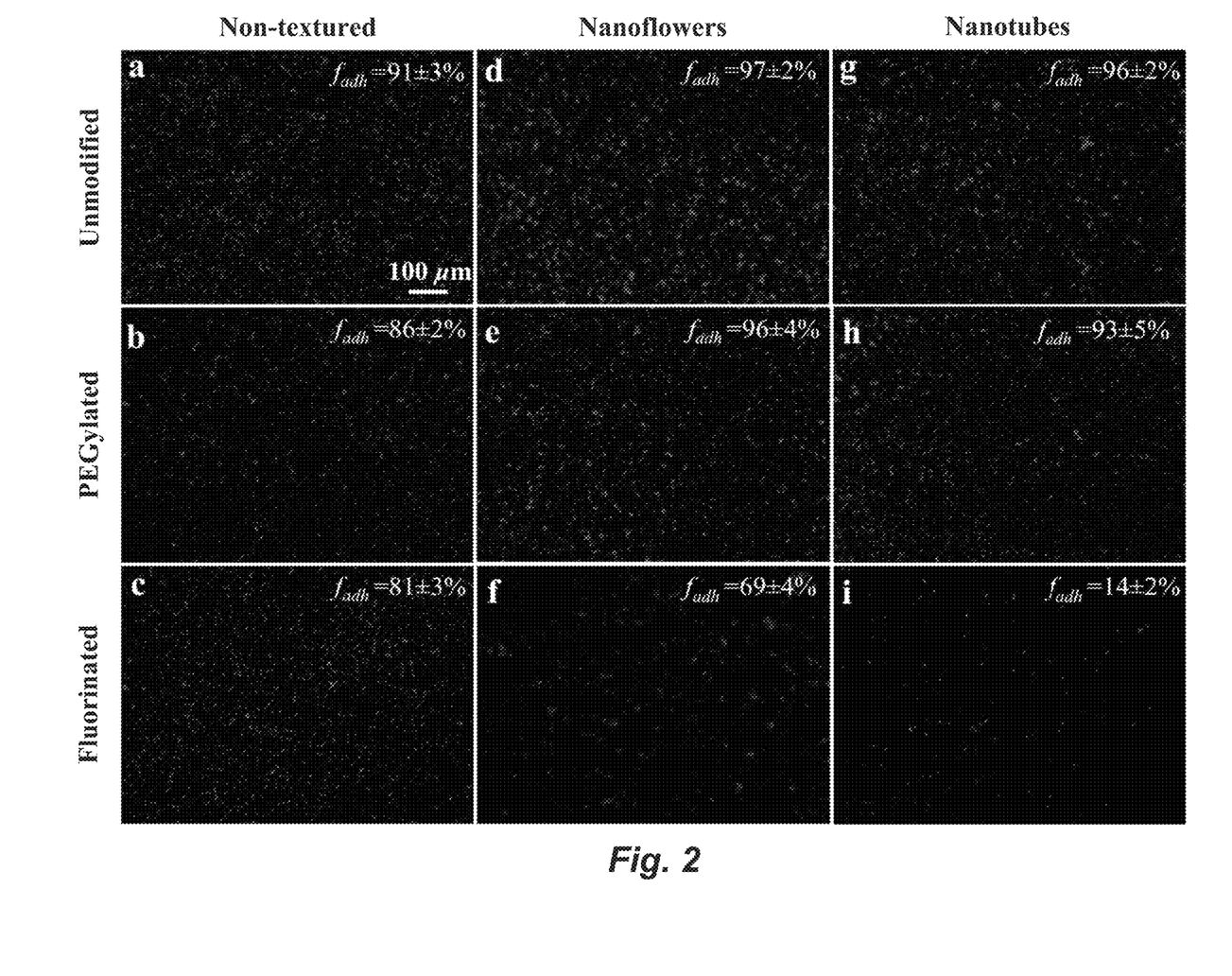
FIG. 2. Fluorescence microscope images showing platelet adhesion for all the titania surfaces. a), b) and c) Unmodified, PEGylated and fluorinated non-textured surfaces, respectively. d), e) and f) Unmodified, PEGylated and fluorinated nanoflower surfaces, respectively. g), h) and i) Unmodified, PEGylated and fluorinated nanotube surfaces, respectively.

After surface fabrication and characterized, the titania samples were sterilized and incubated for 2 h in human blood plasma (see experimental section). In order to evaluate the platelet adhesion, we measured the % area of adhered platelets $f_{adh}$ using fluorescence microscopy (FIG. 2a-2i; see experimental section). Among the non-textured titania surfaces (FIG. 2a-2c), the PEGylated and the fluorinated surfaces resulted in a 5% and 11% lower $f_{adh}$, respectively, compared to the unmodified surfaces. The slightly lower $f_{adh}$ on the PEGylated and the fluorinated surfaces is due to the steric repulsion induced by the water soluble PEG layer and the reduced interaction induced by the low solid surface energy of the fluorocarbons, respectively. Among the unmodified titania surfaces (FIG. 2a, FIG. 2d and FIG. 2g), the nanoflower and nanotube surfaces resulted in 6% and 5% higher $f_{adh}$, respectively, compared to the non-textured surfaces.

The slightly higher $f_{adh}$ on the nanoflower and nanotube surfaces is due to the higher blood-solid interfacial area resulting from the Wenzel state. Similarly, among the PEGylated titania surfaces (FIG. 2b, FIG. 2e and FIG. 2h), the nanoflower and nanotube surfaces resulted in 10% and 7% higher $f_{adh}$, respectively, compared to the non-textured surfaces due to the higher blood-solid interfacial area resulting from the Wenzel state. Among the fluorinated titania surfaces (FIG. 2c, FIG. 2f and FIG. 2i), the superhemophobic nanoflower and superhemophobic nanotube surfaces resulted in 12% and 67% lower $f_{adh}$, respectively, compared to the non-textured surfaces. The lower $f_{adh}$ on the superhemophobic nanoflower and superhemophobic nanotube surfaces is due to the lower blood-solid interfacial area resulting from the Cassie-Baxter state. These platelet adhesion results are consistent with our whole blood clotting results (see Example 5). Among the superhemophobic surfaces, the nanoflower surfaces display significantly higher platelet adhesion compared to the nanotube surfaces. This will be discussed further later.

Figure 3:
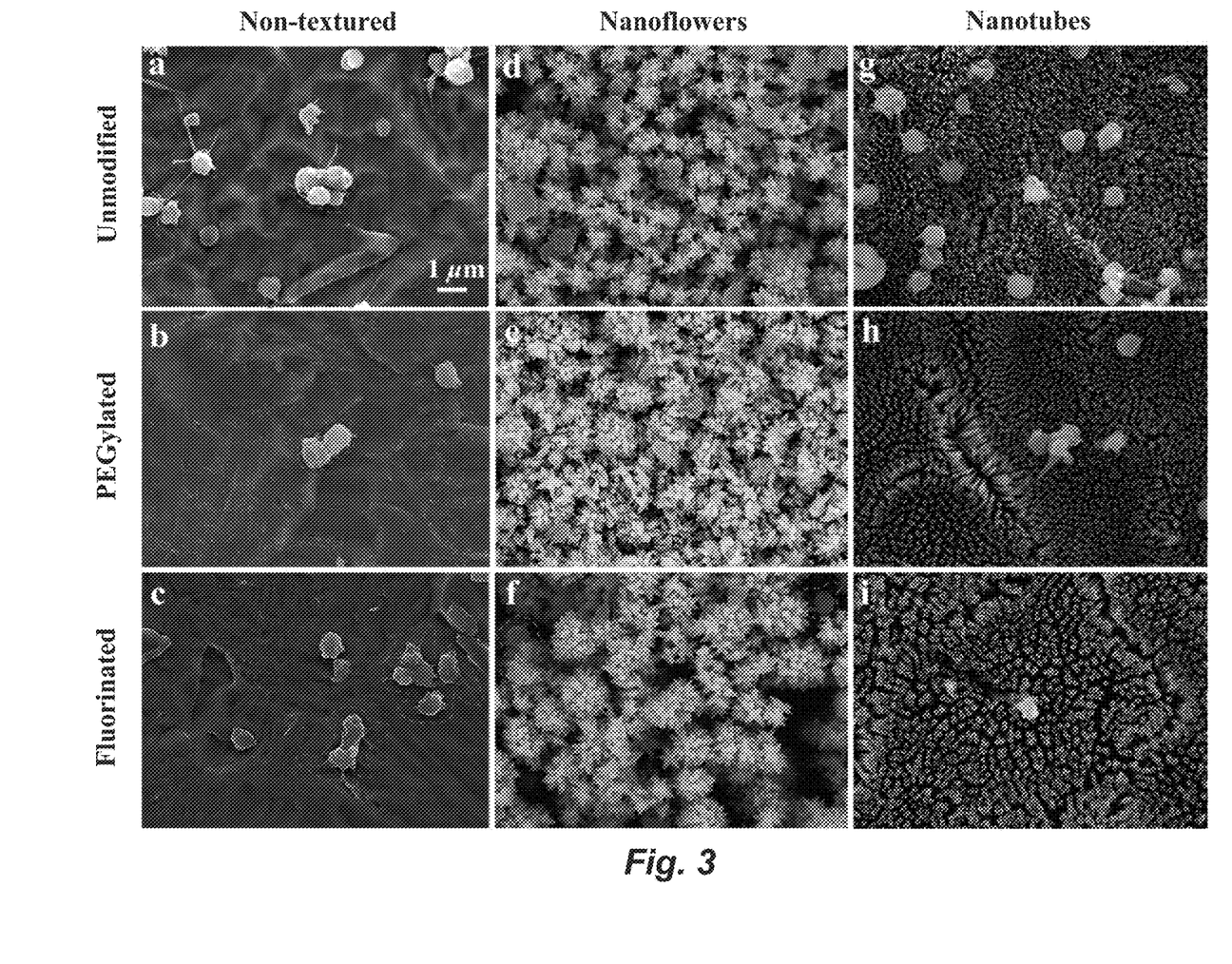
FIG. 3. SEM images showing platelet activation (enclosed by dotted lines in red) on the titania surfaces. a), b) and c) Unmodified, PEGylated and fluorinated non-textured surfaces, respectively. d), e) and f) Unmodified, PEGylated and fluorinated nanoflower surfaces, respectively. g), h) and i) Unmodified, PEGylated and fluorinated nanotube surfaces, respectively.

In order to investigate platelet activation, the titania samples were sterilized and incubated for 2 h in human blood plasma and the fixed surfaces were subsequently studied using a SEM (see experimental section). Typically, platelet activation manifests as change in platelet shape, including dendritic extensions and platelet aggregation. Our results indicate that all unmodified titania surfaces (FIG. 3a, FIG. 3d and FIG. 3g) display both dendritic extensions and aggregation. The PEGylated non-textured surfaces (FIG. 3b) display aggregation, PEGylated nanoflower surfaces (FIG. 3e) display dendritic extensions and the PEGylated nanotube surfaces (FIG. 3h) display both dendritic extensions and aggregation. In other words, all hemophilic surfaces (FIG. 3a, FIG. 3b, FIG. 3d, FIG. 3e, FIG. 3g and FIG. 3h) display platelet activation. In addition, the fluorinated non-textured hemophobic surfaces also display platelet activation via dendritic extensions and aggregation (FIG. 3c). Among the superhemophobic surfaces, the fluorinated nanoflower surfaces (FIG. 3f) display platelet activation via aggregation, but the fluorinated nanotube surfaces display no platelet activation.

While both fluorinated nanoflower surfaces and fluorinated nanotube surfaces are superhemophobic, the fluorinated nanoflower surfaces display significantly higher platelet adhesion and activation compared to the fluorinated nanotube surfaces. This can be explained in terms of robustness of the Cassie-Baxter state for these two surfaces. For titania nanotubes, the feature size (i.e., nanotube diameter) 2R≈0.25 µm and the inter-feature spacing 2D≈0.15 µm, resulting in a highly robust Cassie-Baxter state for human blood plasma with $A^* \approx 815$ (see Example 6). For titania nanoflowers, the feature size (i.e., nanoflower diameter) 2R≈1 µm and the inter-feature spacing 2D≈0.4 µm to 10 µm, resulting in $A^* \approx 266$ to 4 (see Example 6). In other words, due to the large variation in the inter-feature spacing, there is a large variation in the robustness of the Cassie-Baxter state for the fluorinated nanoflower surfaces.

When such fluorinated nanoflower surfaces are subjected to shaking during incubation, the human blood plasma can easily breakthrough and transition from the Cassie-Baxter state to the Wenzel state in local pockets with low robustness (e.g., $A^* \approx 4$) of the Cassie-Baxter state. These local Wenzel states lead to higher blood-solid interfacial area and consequently higher platelet adhesion and activation for the fluorinated nanoflower surfaces compared to the fluorinated nanotube surfaces with a complete and robust Cassie-Baxter state. These results indicate that not all superhemophobic titania surfaces lead to significantly reduced platelet adhesion and activation. Further, our analysis indicates that only those superhemophobic surfaces with a robust Cassie-Baxter state display significantly lower platelet adhesion and activation compared to hemophobic and hemophilic surfaces.

Summary

Figure 7:
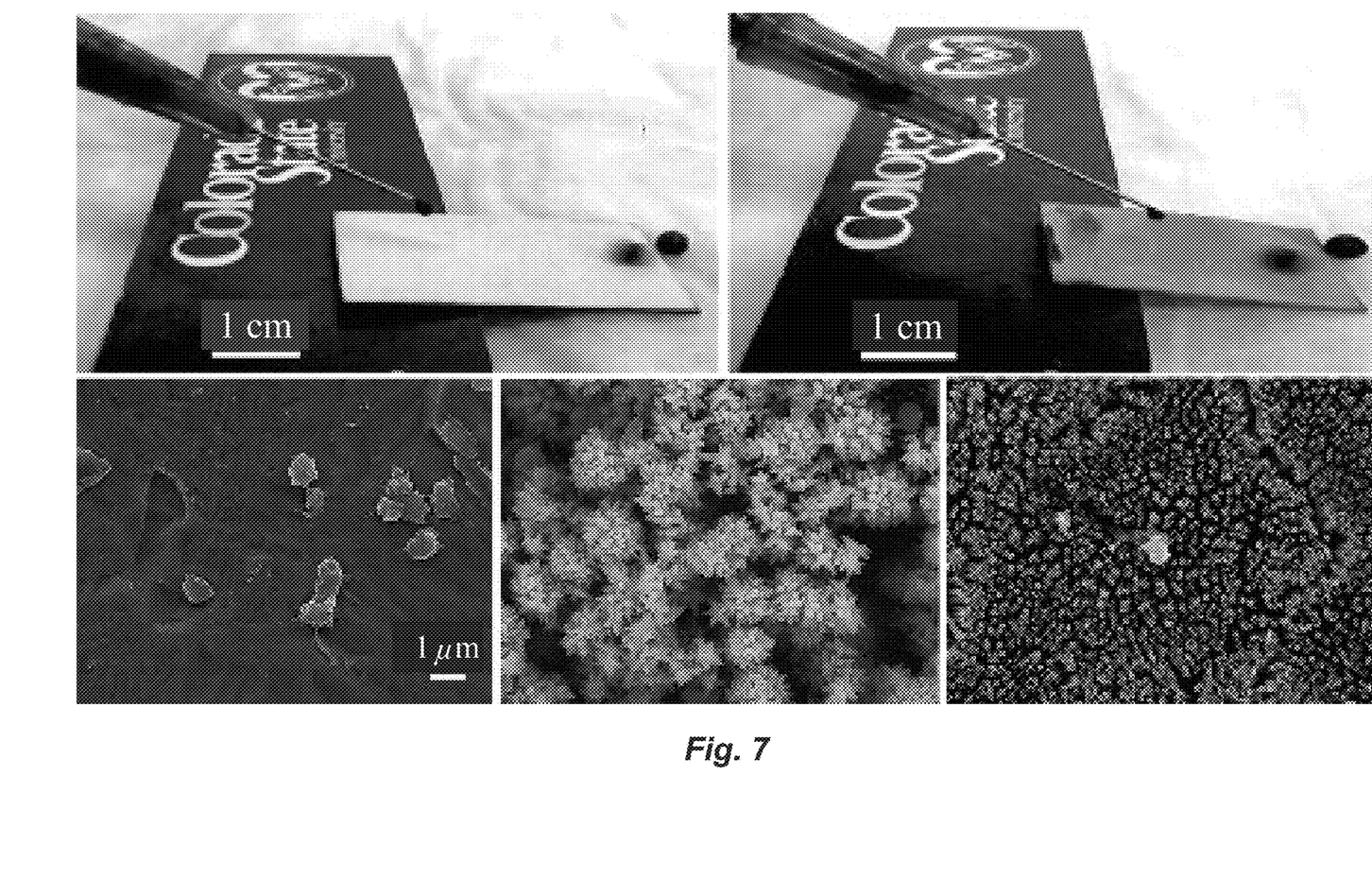
FIG. 7. Hemocompatibility of Superhemophobic Titania Surfaces.

We fabricated hemophilic, hemophobic and superhemophobic titania surfaces by employing three different morphologies—non-textured, nanoflowers and nanotubes—and for each morphology, three different surface chemistries—unmodified, PEGylated and fluorinated. For each of our titania surfaces, we characterized the wettability using contact angle goniometry, the surface chemistry using XPS, and platelet adhesion and activation using fluorescence microscopy and SEM. Our results indicate that not all superhemophobic titania surfaces lead to significantly reduced platelet adhesion and activation. Our analysis indicates that only those superhemophobic surfaces with a robust Cassie-Baxter state display significantly lower platelet adhesion and activation compared to hemophobic and hemophilic surfaces (FIG. 7). We envision that the understanding gained through this work will lead to the fabrication of improved hemocompatible, superhemophobic medical implants.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Fabrication of Titania Surfaces with Different Morphologies

Non-textured titania surfaces were fabricated by dipping titanium sheets in 1:1:20 $HF:H_2O_2:H_2O$ (by volume) oxidizing solution for 10 seconds. Titania nanotube surfaces were fabricated by electrochemical anodization with a titanium anode and platinum cathode in a 95:2:3 $DEG:HF:H_2O$ (by volume) electrolyte at 60 V for 24 h followed by annealing in air at 530° C. for 6 h. Titania nanoflower surfaces were fabricated via hydrothermal synthesis by immersing a titanium sheet in 20 mM HF in a PTFE-lined stainless steel autoclave at 100° C. for 6 h. All samples were rinsed thoroughly with DI water and dried with nitrogen.

Measurement of Surface Roughness.

The root mean square roughness $R_{rms}$ of the surfaces was measured using an optical profilometer (Zygo Zescope). At least three measurements were performed on each surface.

Example 2. Modification of Titania Surfaces with Different Surface Chemistries

The titania surfaces were fluorinated via vapor phase silanization with 200 µl of heptadecafluoro-1,1,2,2-tetrahydrodecyl trichlorosilane (Gelest) at 120° C. for 1 hour. The titania surfaces were PEGylated via liquid phase silanization with 2 vol % 2-[Methoxy (Polyethyleneoxy) propyl] trimethoxysilane (Gelest) in ethanol for 24 h. We estimated the solid surface energy of our surfaces using Owens-Wendt analysis. The solid surface energy of unmodified, PEGylated and fluorinated titania surfaces are $\gamma_{sv}=40$ mN m$^{-1}$, $\gamma_{sv}=51$ mN m$^{-1}$ and $\gamma_{sv}=11$ mN m$^{-1}$, respectively.

Characterization of Surface Chemical Composition.

X-ray photo-electron spectroscopy (XPS) analysis was conducted on the surfaces using a PHI-5800 spectrometer (Physical Electronics). XPS was conducted using a monochromatic Al—K X-ray source operated at 15 kV and photoelectrons were collected at a takeoff angle of ~45° relative to the sample surface.

Measurement of Contact Angles and Roll Off Angles.

The contact angles and roll-off angles were measured using a contact angle goniometer (Ramé-Hart 200-F1). The contact angles were measured by advancing or receding ~5 µl droplets on the surface using a micrometer syringe (Gilmont). The roll-off angles were measured by tilting the stage until the ~5 µl droplet rolled off from the surface. At least six measurements were performed on each surface. The errors in contact angle and roll-off angle were ±1° and ±0.5°, respectively.

Example 3. Fabrication of Titania Nanotubes and Titania Nanoflowers Surfaces

Figure 4:
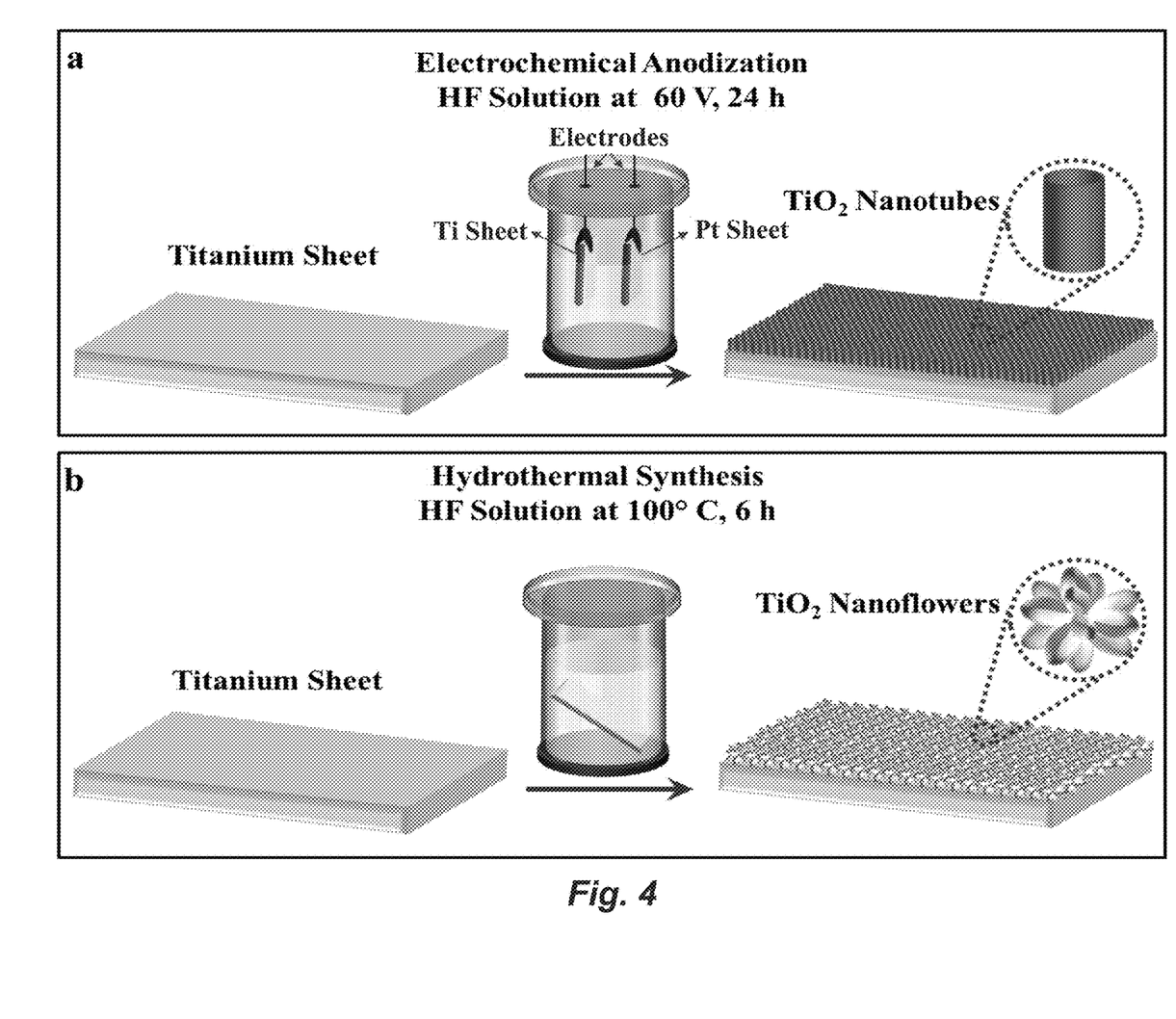
FIG. 4. Schematic depicting the fabrication of a) titania nanotubes and b) titania nanoflowers.

Titanium sheets (8 mm long×8 mm wide×0.8 mm thick) were cleaned with soap, followed by sonication in acetone and isopropanol and then dried with nitrogen gas. For fabricating titania nanotubes, a two-electrode cell was used with the cleaned titanium sample as the anode and a platinum sheet as the cathode (FIG. 4a). The electrolyte was prepared by mixing 95% diethylene glycol with 2% hydrofluoric acid HF and 3% de-ionized water. All experiments were carried out at room temperature, at 60 V for 24 h. After anodization, the samples were rinsed with isopropanol and dried with nitrogen gas. Subsequently, the substrates were annealed in oxygen ambient at 530 C for 6 h to obtain the titania nanotube arrays. For fabricating titania nanoflowers, the cleaned titanium sheet was placed in a PTFE-lined stainless steel autoclave containing 20 mM hydrofluoric acid. The autoclave was sealed and the Ti sheets were etched under hydrothermal conditions at 100° C. for 6 h (FIG. 4b).

After hydrothermal synthesis, the samples were rinsed with thoroughly with DI water and dried with nitrogen gas.

Example 4. Incubation of Titania Surfaces in Human Blood Plasma

Whole blood was drawn from a healthy individual with care to avoid locally activated platelets and centrifuged in vials at 300 g for 15 min to separate the human blood plasma from the erythrocytes. Sterilized titania surfaces (washed in 70% ethanol, then in PBS and air dried) were incubated in 1 ml of the plasma in a 24-well plate at 37° C. and 5% $CO_2$ on a horizontal shaker plate (100 rpm) for 2 h.
Characterization of Platelet Adhesion with Fluorescence Microscopy.

After incubation of titania surfaces in human blood plasma, the unadhered platelets were removed by gently rinsing with PBS. Adhered platelets were fixed in a 3.7 wt % formaldehyde in PBS solution for 15 min and subsequently washed multiple times with PBS. The cell membranes were permeabilized using 1% Triton-X in PBS for 3 min. The titania surfaces were then incubated in PBS solutions containing 500 µl of rhodamine phalloidin (cytoskeleton red stain) for 25 min. The surfaces were subsequently rinsed with PBS and imaged using a fluorescence microscope (Zeiss). The % area of adhered platelets $f_{adh}$ was obtained using ImageJ software.
Characterization of Morphology and Platelet Activation with Scanning Electron Microscopy.

The morphology of the titania non-textured, nanoflower and nanotube surfaces and platelet activation of all titania surfaces were imaged using scanning electron microscope (JEOL JSM-6500F) at 15 kV. Prior to imaging the platelet activation, the incubated titania surfaces were gently rinsed with PBS to remove the unadhered platelets. The adhered platelets were first fixed in a primary fixative (6% glutaraldehyde, 0.1 M sodium cacodylate, and 0.1 M sucrose) for 45 min and then in a secondary fixative (primary fixative without glutaraldehyde) for 10 min. The surfaces were then dehydrated in consecutive solutions of ethanol (35%, 50%, 70%, and 100%) for 10 min each and finally in a solution of hexamethyldisilazane for 10 min. The surfaces were then air-dried and imaged.

Example 5. Comparison of Whole Blood Clotting

We compared the whole blood clotting on our hemophilic, hemophobic and superhemophobic titania surfaces by measuring the free hemoglobin concentration. In a typical experiment, whole human blood was drawn from a healthy individual, and 5 µL of the blood was immediately placed on unmodified non-textured, nanoflower and nanotube titania surfaces as well as fluorinated non-textured, nanoflower and nanotube titania surfaces contained in a 48-well plate. The blood was allowed to clot on the surfaces for 15 min at room temperature. Subsequently, 500 µL of deionized (DI) water was added to each well. The surfaces were gently agitated for 30 s and left in DI water for 5 min to release free hemoglobin from red blood cells that were not trapped in the thrombus. To measure the free hemoglobin concentration, 200 µL of the solution in each well was then transferred into a 96-well plate. The absorbance of the solution with free hemoglobin was measured at a wavelength of 540 nm using a plate reader. The value of absorbance is directly proportional to the concentration of free hemoglobin in DI water and is an inverse measure of the degree of clotting.

Our results (see Table 2) indicate that the amount of free hemoglobin is slightly higher (i.e., blood clotting is slightly lower) for the fluorinated non-textured titania surfaces compared to the unmodified non-textured titania surfaces. Further, the amount of free hemoglobin on unmodified textured (i.e., nanoflower and nanotube) titania surfaces is lower (i.e., blood clotting is higher) compared to unmodified non-textured titania surfaces. Due to the superhemophobicity of the fluorinated nanoflower and fluorinated nanotube surfaces, blood droplets immediately rolled off and did not remain on these surfaces even when they are horizontal, possibly indicating low potential for blood clotting. However, rigorous blood clotting experiments via immersion could not be conducted because our substrates are not textured on all sides. These whole blood clotting results are consistent with our platelet adhesion and activation results.

TABLE 2

Free hemoglobin concentration (measured as absorbance) after clotting experiments on various surfaces.

| Surface | Free hemoglobin conc. (measured as absorbance) | |
|---|---|---|
| | Before clotting | After clotting |
| Unmodified non-textured surface | 3.0 ± 0.2 | 0.6 ± 0.1 |
| Fluorinated non-textured surface | 3.0 ± 0.2 | 1.0 ± 0.3 |
| Unmodified nanoflower surface | 3.0 ± 0.2 | 0.5 ± 0.2 |
| Unmodified nanotube surface | 3.0 ± 0.2 | 0.5 ± 0.2 |

Example 6. Derivation of the Robustness Factor, A*

Figure 5:
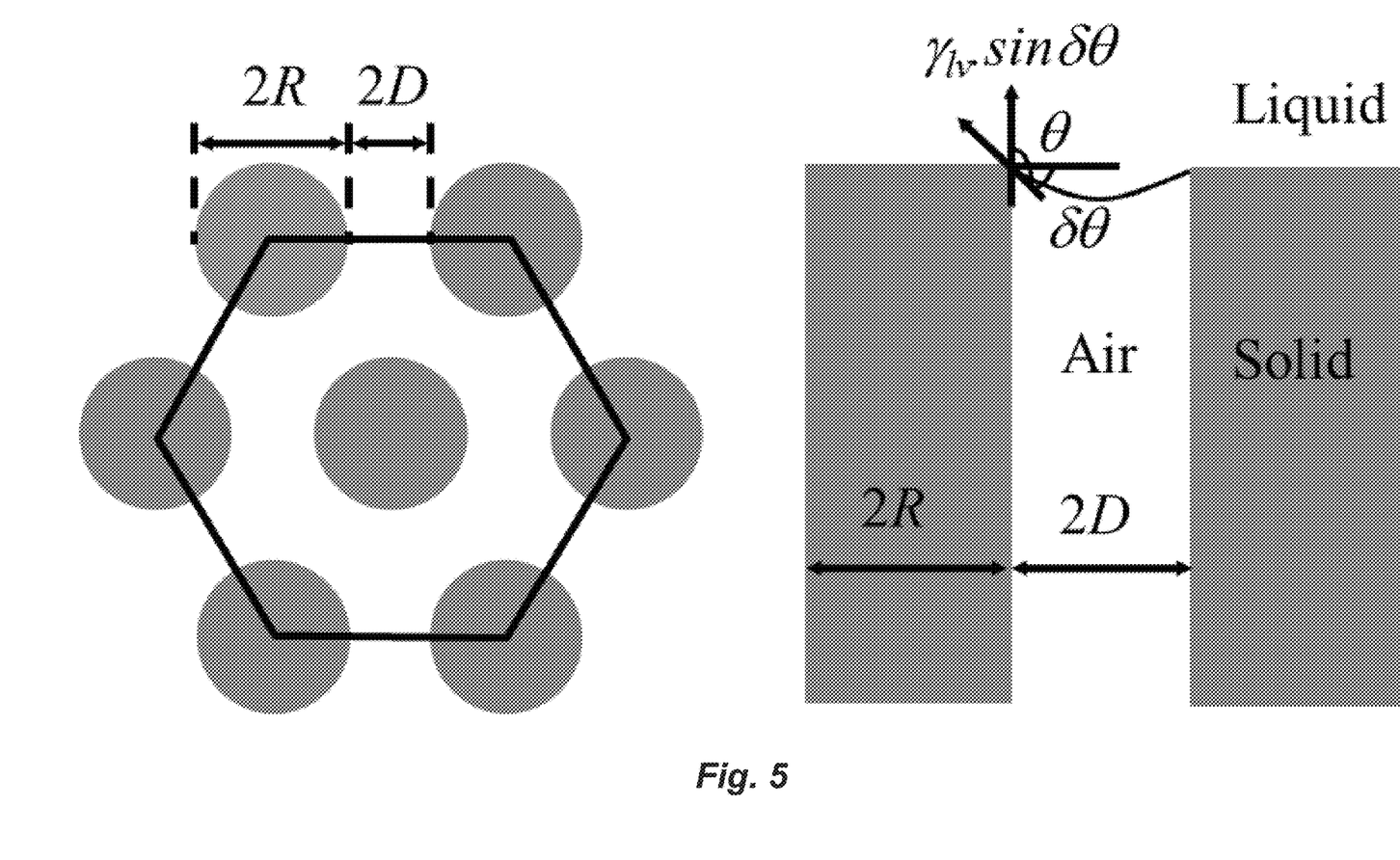
FIG. 5. A textured solid composed of hexagonally packed pillars with diameter 2R and inter-feature spacing of 2D.

When a liquid is in the Cassie-Baxter state on a textured solid (see FIG. 5), a generalized force balance across the composite (solid-liquid-air) interface can be written as:

$$P_{breakthrough}(\text{Interfacial area}) = \gamma_{lv}(\text{Contact line length}) \sin \delta\theta \quad (1)$$

Here, $P_{breakthrough}$ is the breakthrough pressure (corresponding to the transition from the Cassie-Baxter state to the Wenzel state), $\gamma_{lv}$ is the surface tension of the liquid and $\delta\theta$ is the sag angle of the liquid-vapor interface. For a textured solid composed of hexagonally packed pillars, Equation (1) can be written as:

$$P_{breakthrough}(6\sqrt{3}(R+D)^2) \approx \gamma_{lv}(6\pi R)\sin \delta\theta \quad (2)$$

Here, 2R is the pillar diameter and 2D is the inter-feature spacing. Solving for $P_{breakthrough}$, we get:

$$P_{breakthrough} \approx \left| \frac{\gamma_{lv} \pi R \cos\theta}{\sqrt{3}(R+D)^2} \right| \quad (3)$$

Here, θ is the Young's contact angle. The reference pressure $P_{ref}$ (i.e., the minimum possible pressure difference across the composite interface for millimetric or larger liquid droplets or puddles on extremely non-wetting textured surfaces), is given as:

$$P_{ref} = \frac{2\gamma_{lv}}{l_{cap}} \quad (4)$$

Here, $l_{cap}$ is the capillary length, given as:

$$l_{cap} = \sqrt{\frac{\gamma_{lv}}{\rho g}} \quad (5)$$

Here, r is the density of the liquid and g is the acceleration due to gravity. The robustness factor A* is obtained by combining Equations (3) and (4) as:

$$A^* = \frac{P_{breakthrough}}{P_{ref}} \approx \left| \frac{\pi R l_{cap} \cos\theta}{2\sqrt{3}(R+D)^2} \right| \quad (6)$$

Robustness Factor A* Values for Superhemophobic Nanoflower and Nanotube Surfaces.

Figure 6:
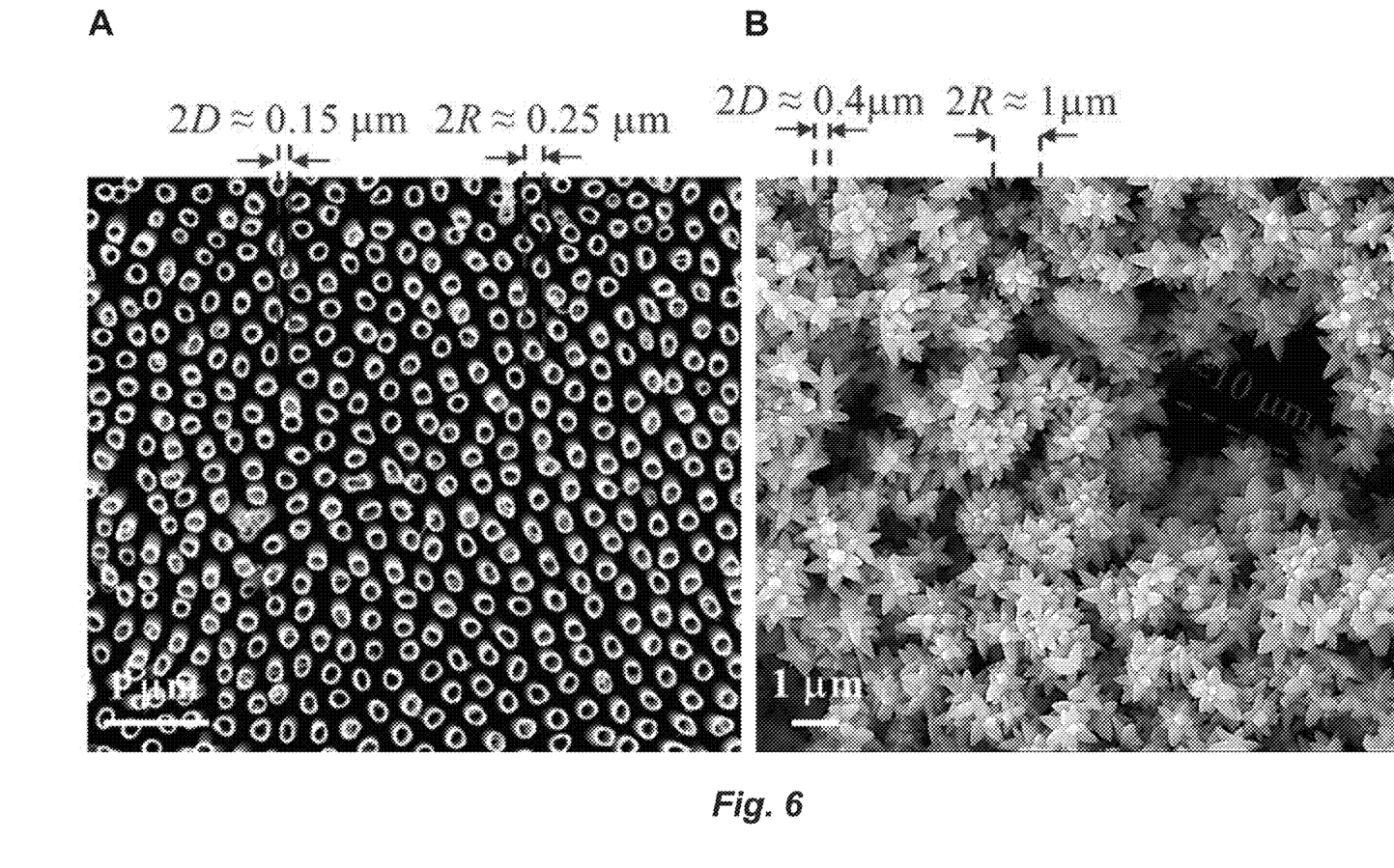
FIG. 6. SEM images of a) Titania nanotubes and b) Titania nanoflowers.

The robustness factor A* values for superhemophobic surfaces titania nanoflowers and titania nanotubes are calculated using Equation (6). For human blood plasma, the density $\rho=1025$ kg m$^{-3}$ and the surface tension $\gamma_{lv}=56$ mN m$^{-1}$. Using Equation (5), for human blood plasma, we obtain the capillary length $l_{cap}=2.36$ mm. We assume that the Young's contact angle of human blood plasma on fluorinated titania surface is approximately equal to the static contact angle θ=97° of human blood plasma on the non-textured fluorinated titania surface (see Table 1). For titania nanotubes (FIG. 6a), the feature size (i.e., nanotube diameter) 2R≈0.25 μm and the inter-feature spacing 2D≈0.15 μm. For titania nanoflowers (FIG. 6b), the feature size (i.e., nanoflower diameter) 2R≈1 μm, but there is a significant variation in the inter-feature spacing 2D≈0.4 μm to 10 μm. Using the above listed values, we estimated the robustness factor A* for superhemophobic titania nanotube and titania nanoflower surfaces (see Table 3).

TABLE 3

The estimated robustness parameter A* for titania nanotubes and nanoflowers.

| Texture | 2R (μm) | 2D (μm) | A* |
|---|---|---|---|
| Nanotubes | 0.25 | 0.15 | 815 |
| Nanoflowers | 1 | 0.4 to 10 | 266 to 4 |

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A superhemophobic surface comprising:
    nanotubes of fluorine anodized titania, the surface having an arrayed nanotube textured morphology, wherein the anodized titania is annealed and fluorinated with fluorinated ($C_8$-$C_{18}$)alkyl moieties;
    the nanotubes have a wall thickness of about 20 nm and an opening at the end toward the surface; and
    the nanotube textured morphology has a feature diameter (2R) of less than about 1 μm and an inter-feature spacing (2D) of less than about 10 μm.

2. The superhemophobic surface of claim 1 wherein the inter-feature spacing (2D) is about 0.05 μm to 5 μm.

3. The superhemophobic surface of claim 1 wherein the surface has a Cassie-Baxter robustness factor (A*) of at least about 5 for blood.

4. The superhemophobic surface of claim 1 wherein the textured morphology has a feature diameter (2R) of about 0.05 μm to about 0.5 μm and an inter-feature spacing (2D) of about 0.05 μm to less than 5 μm.

5. The superhemophobic surface of claim 1 wherein the fluorinated ($C_8$-$C_{18}$)alkyl is a heptadecafluoro-1,1,2,2-tetrahydrodecyl moiety.

6. The superhemophobic surface of claim 3 wherein A* is about 50 to about 5000 and the inter-feature spacing (2D) is about 0.05 μm to 1 μm.

7. The superhemophobic surface of claim 6 wherein the surface energy ($\gamma_{sv}$) of the superhemophobic surface is less than about 20 mN m$^{-1}$.

8. The superhemophobic surface of claim 1 wherein the superhemophobic surface is biocompatible.

9. The superhemophobic surface of claim 8 wherein a blood platelet that adheres to the superhemophobic surface having a textured morphology does not manifest in platelet aggregation, or dendritic extensions.

10. The superhemophobic surface of claim 9 wherein the % area of blood platelets ($f_{adh}$) that adheres to the superhemophobic surface is about 15% to about 95% lower than the $f_{adh}$ of a fluorinated titania surface having a non-textured morphology.

11. The superhemophobic surface of claim 1 wherein a drop of blood on the superhemophobic surface has a contact angle of greater than about 155°.

12. The superhemophobic surface of claim 11 wherein the drop of blood on the superhemophobic surface has a roll off angle of less than about 5°.

13. A superhemophobic surface comprising:
    nanotubes of fluorine anodized titania, the surface having an arrayed nanotube textured morphology, wherein the anodized titania is annealed and fluorinated with fluorinated ($C_8$-$C_{18}$)alkyl moieties;
    the nanotubes have an opening at the end toward the surface wherein the opening is about 100 nm to about 150 nm wide; and
    the nanotube textured morphology has a feature diameter (2R) of less than about 1 μm and an inter-feature spacing (2D) of less than about 10 μm.

14. The superhemophobic surface of claim 13 wherein the nanotubes have a wall thickness of about 20 nm.

15. A method of fabricating a biocompatible medical device comprising forming the superhemophobic surface of claim 1 on a medical device, wherein the medical device comprising the superhemophobic surface can be implanted in a subject and is biocompatible with the subject wherein formation of a blood clot on the medical device comprising the superhemophobic surface is negligible.

16. A method of fabricating a superhemophobic surface according to claim 1 comprising:
    a) anodizing an oxidized titanium substrate in an electrolyte comprising hydrofluoric acid and diethylene glycol at a voltage sufficient to form a titania nanotube array;
    b) annealing the titania nanotube array in a gas comprising oxygen; and c) fluorinating the titania nanotube array to form a superhemophobic surface;

wherein the superhemophobic surface has a Cassie-Baxter robustness factor (A*) of at least about 5 for blood.

17. The method of claim 16 wherein the % area of blood platelets ($f_{adh}$) that adheres to the superhemophobic surface is at least about 20% lower than the $f_{adh}$ of a fluorinated non-textured titania surface.

18. The method of claim 16 wherein a blood platelet that adheres to the superhemophobic surface does not manifest in platelet activation.

19. The method of claim 16 wherein the electrolyte comprises 2% v/v hydrofluoric acid and 95% v/v diethylene glycol and the voltage is about 60 V.

* * * * *